United States Patent [19]
de Haan

[11] Patent Number: 5,907,084
[45] Date of Patent: May 25, 1999

[54] VIRUS RESISTANT OR TOLERANT CELLS

[75] Inventor: Petrus Theodorus de Haan, Enkhuizen, Netherlands

[73] Assignee: Novartis Finance Corporation, New York, N.Y.

[21] Appl. No.: 08/624,581

[22] PCT Filed: Oct. 5, 1994

[86] PCT No.: PCT/EP94/03295

§ 371 Date: Apr. 3, 1996

§ 102(e) Date: Apr. 3, 1996

[87] PCT Pub. No.: WO95/09920

PCT Pub. Date: Apr. 13, 1995

[30] Foreign Application Priority Data

Oct. 6, 1993 [GB] United Kingdom .................... 9320548

[51] Int. Cl.⁶ ....................................................... A01H 1/04
[52] U.S. Cl. .......................... 800/205; 800/250; 800/255; 536/23.1; 536/24.5; 435/320.1; 435/411; 435/414
[58] Field of Search ................................. 435/172.3, 240.4, 435/252.3, 410, 419, 69.1, 320.1, 414, 411; 536/24.5, 23.2, 23.1, 23.72; 800/200, 205, 250, 255

[56] References Cited

U.S. PATENT DOCUMENTS 5,316,930  5/1994  Loesch-Fries et al. .............. 435/172.3
5,503,999  4/1996  Jilka et al. ........................... 435/172.3
5,589,612  12/1996  Jilka et al. ............................... 800/205

OTHER PUBLICATIONS

Lawson et al. Bio/Technology, vol. 8, pp. 127–134, 1990.
Yie et al. Molecular Plant–Microbe Interactions, vol. 5 (6), pp. 460–465, 1992.
Lamb et al. Journal of General Virology, vol. 71, pp. 2257–2264, 1990.
Tabler et al. Gene, vol. 108, pp. 175–183, 1991.
Milligan et al. Journal of Medicinal Chemistry, vol. 36 (14), pp. 1923–1937, Jul. 9, 1993.

*Primary Examiner*—James Ketter
*Assistant Examiner*—Irem Yucel
*Attorney, Agent, or Firm*—Thomas Hoxie; J. Timothy Meigs

[57] ABSTRACT

A nucleotide sequence comprising a transcriptional regulatory sequence and a sequence contiguous therewith and under the transcriptional control thereof, which contiguous sequence encodes an RNA which consists of a plurality of sub-sequences, characterized in that at least two of the sub-sequences have the sequences of viral RNAs and the RNA contains at least one translational stop codon located upstream of the 3' terminal sub-sequence. It is preferred that at least one of the sub-sequences is in an anti-sense configuration with respect to virus RNA, and that the contiguous sequence encodes mRNA. The invention also includes, inter alia, the use of such a sequence in the generation of virus resistant or tolerant plants, and such plants comprising the sequence.

27 Claims, 2 Drawing Sheets

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 2959 base pairs
        (B) TYPE: nucleic acid
        (C) STRANDEDNESS: double
        (D) TOPOLOGY: unknown     (iii) HYPOTHETICAL: NO     (iii) ANTI-SENSE: NO     (vi) ORIGINAL SOURCE:
        (A) ORGANISM: Chimeric sequence     (xi) SEQUENCE DESCRIPTION: SEQ ID NO:1:

```
GGATCCTGCA GAGCAATTGT GTCAATTTTA TTCAAAAACC TAATACTCAG CAATACAAAT      60

CATCACATTA ACAGGATAAG TAACGACCGC GGTCTACAGT GTTGCACTTT CTCACCTTGA     120

ATCTTATCTC TCGAGAAAGG TCTAGATCTA AACTACCACC ATGTCTAAGG TCAAGCTCAC     180

AAAAGAAAAC ATTGTCTCTC TTTTGACTCA ATCTGAGGAT GTTGAGTTTG AAGAAGACCA     240

GAACCAGGTT GCATTCAACT TTAAGACTTT TTGTCAGGAA AATCTTGACC TGATTAAGAA     300

AATGAGTATC ACTTCATGTT TGACTTTCTT GAAGAATCGC CAAAGCATCA TGAAAGTTGT     360

GAAACAAAGT GATTTTACTT TTGGCAAGGT CACGATAAAG AAAAATTCAG AGAGGGTTGA     420

AGCTAAAGAC ATGACTTTCA GAAGGCTTGA TAGCATGATA AGAGTGAAAC TCATAGAAGA     480

GACTGCAAAC AATGAGAATC TTGCTATCAT CAAGGCAAAA ATTGCCTCCC ATCCTTTGGT     540

CCAAGCTTAC GGGCTGCCTT TGGACGATGC AAAATCTGTG AGACTTGCCA TAATGCTTGG     600

AGGTAGTATC CCTCTCATTG CTTCTGTTGA CAGTCTCGAA ATGATCAGTG TTGTTCTTGC     660

CATATATCAA GATAGTCAAG TACAGGAGTT AGGGATTGAA CCAACTAAGT ACAACACTAA     720

GGAAGCTCTG GGGAAGGTTT GCACTGTGCT GAAAAGCAAA GGATTTACAA TGGATGATGC     780

ACAAGATAAC AAAGGGAAAG AATATGCTAA GATACTCAGT TCTTGCAATC CCAATGCTAA     840

GGGAAGCATT GCTATGGACT ATTACAGTGA CAATCTTGAG AAGTTCTATG AAATGTTTGG     900

AGTCAAGAAA GAGGCCAAGA TTGCTGGTGT TGCATAAAAG CTTCTTTGTG TTAATTAAGA     960

GATGCATAAT ACTAAGTGTG GGGTACCCTT AACACTCAGT CTTACAAATC ATCACATTAA    1020

GAACCTAAGA AACGACTGCG GGATACAGAG TTGCACTTTC GCACCTTGAG TTACATACGG    1080

TCAAAGCATA TAACAACTTT TACGATCATC ATGTCTAAGG TTAAGCTCAC TAAGGAAAGC    1140

ATTGTTGCTT TGTTGACACA AGGCAAAGAC CTTGAGTTTG AGGAAGATCA GAATCTGGTA    1200

GCATTCAACT TCAAGACTTT TTGTCTGGAA AACATCGACC AGATCAAGAA GATGAGCGTT    1260

ATTTCATGTC TGACATTCCT AAAGAATCGT CAGAGCATAA TGAAGGTTAT TAAGCAAAGC    1320

GATTTTACTT TTGGTAAAAT TACCATAAAG AAAACTTCAG ACAGGATTGG AGGCACTGAC    1380

ATGACCTTCA GAAGGCTTGA TAGCTTGATC AGGGTCAGGC TTGTTGAAGA AACTGGGAAT    1440
```

```
TCTGAGAATC TCAATACTAT CAAATCTAAG ATTGCTTCCC ATCCTTTGAT TCAAGCCTAT    1500

GGATTACCTC TCGATGATGC AAAGTCTGTG AGACTTGCCA TAATGCTGGG AGGTAGCTTA    1560

CCTCTTATTG CTTCAGTTGA TAGCTTTGAG ATGATCAGTG TTGTCTTGGC TATATATCAG    1620

GATGCAAAAT ACAAGGACCT CGGGATCGAC CCAAAGAAGT ATGACACCAA GGAAGCCTTA    1680

GGAAAAGTTT GCACTGTGCT GAAAAGCAAA GCATTTGAAA TGAATGAAGA TCAGGTGAAG    1740

AAGGGGAAAG AGTATGCTGC TATACTTAGC TCCAGCAATC CTAATGCTAA AGGGAGTGTT    1800

GCTATGGAAC ATTACAGTGA AACTCTTAAC AAGTTCTATG AAATGTTCGG GGTTAAAAAG    1860

CAGGCAAAAC TCGCAGAACT TGCTTGAAAG CAGCTGTAAG TTAAATTATA AAAAGCCTA     1920

TAAATATATA AAGCTTATCG ATACCGTCGA CCTCGAGGGG GGGCCCGGTA CCGAGCTCGC    1980

TGCAGAGCAA TTGTGTCAAT TTTATTCAAA AACATACTAC TCAGCAACAC AAATCATCAC    2040

ATTGCCAGGA TAAGTAACGA CTGCGGTCTA CAGAGTCGTA CTTTCTTACC TTGAATCACA    2100

TCTCTCGAGA GCGGTCTAGA TCTACACTGC CAAAAATGTC TAAGGTCAAG CTCACCAGAG    2160

AGAACATTAT CTCTCTTCTA ACTCAGGCTG GAGAAATCGA GTTTGAAGAA GATCAAATCA    2220

AGGCTACATT CAACTTCGAA GACTTTTGCG GAGAAAATCT TGATTCAATC AAGAAAATGA    2280

GCATTACCTC ATGTTTGACT TTCCTGAAAA ATCGCCAGAG CATCATGAAA GTTGTGAACC    2340

TTTGTGATTT TACCTTTGGG AAAATCACAA TCAAAAAGAA TTCTGGAAGG GTTGGAGCTA    2400

ATGATATGAC TTTCAGAAGG CTTGATAGCA TGATAAGAGT TAAGCTGATT GAAGAAACTG    2460

GAAAAGCAGA AAACCTTGCT ATTATCAAGT CTAAGATTGC CTCTCATCCT CTTGTTCAAG    2520

CTTATGGTCT GCCTCTGACA GATGCAAAGT CTGTAAGGCT TGCCATAATG CTAGGAGGTA    2580

GTATCCCTCT GATTGCTTCT GTGGACAGCT TTGAAATGAT CAGCATCATC CTTGCCATAT    2640

ACCAAGATGC TAAATATAAA GATCTTGGAA TTGAACCTTC GAAGTATAAC ACTAAAGAAG    2700

CTTTAGGAAA AGTCTGCACT GTGCTGAAAA GCAAAGGATT TACAATGGAT GAAGAGCAAG    2760

TGCAGAAAGG GAAAGAATAT GCTACAATAC TCAGCTCTTG CAATCCTAAT GCTAAAGGAA    2820

GCATTGCTAT GGAACATTAC AGTGAGCATC TTGACAAATT CTATGCAATG TTCGGAGTAA    2880

GGAAAGAAGC CAAAATTTCA GGTGTTGCAT GAAAGCTTCT TAAAATCTAT TTAAGAGATG    2940

AGTATTGTAG GCGGGATCC                                                 2959

(2) INFORMATION FOR SEQ ID NO:2:

(i) SEQUENCE CHARACTERISTICS:
         (A) LENGTH: 2899 base pairs
         (B) TYPE: nucleic acid
         (C) STRANDEDNESS: double
         (D) TOPOLOGY: unknown (iii) HYPOTHETICAL: NO (iii) ANTI-SENSE: NO (vi) ORIGINAL SOURCE:
         (A) ORGANISM: Chimeric sequence (xi) SEQUENCE DESCRIPTION: SEQ ID NO:2:

GGATCCTGCA GAGCAATTGT GTCAATTTTA TTCAAAAACC TAATACTCAG CAATACAAAT      60

CATCACATTA ACAGGATAAG TAACGACCGC GGTCTACAGT GTTGCACTTT CTCACCTTGA     120

ATCTTATCTC TCGAGAAAGG TCTAGATCTA AACTACCACC ATGTCTAAGG TCAAGCTCAC     180

AAAAGAAAAC ATTGTCTCTC TTTTGACTCA ATCTGAGGAT GTTGAGTTTG AAGAAGACCA     240

GAACCAGGTT GCATTCAACT TTAAGACTTT TTGTCAGGAA AATCTTGACC TGATTAAGAA     300
```

```
AATGAGTATC ACTTCATGTT TGACTTTCTT GAAGAATCGC CAAAGCATCA TGAAAGTTGT     360

GAAACAAAGT GATTTTACTT TTGGCAAGGT CACGATAAAG AAAAATTCAG AGAGGGTTGA     420

AGCTAAAGAC ATGACTTTCA GAAGGCTTGA TAGCATGATA AGAGTGAAAC TCATAGAAGA     480

GACTGCAAAC AATGAGAATC TTGCTATCAT CAAGGCAAAA ATTGCCTCCC ATCCTTTGGT     540

CCAAGCTTAC GGGCTGCCTT TGGACGATGC AAAATCTGTG AGACTTGCCA TAATGCTTGG     600

AGGTAGTATC CCTCTCATTG CTTCTGTTGA CAGTCTCGAA ATGATCAGTG TTGTTCTTGC     660

CATATATCAA GATAGTCAAG TACAGGAGTT AGGGATTGAA CCAACTAAGT ACAACACTAA     720

GGAAGCTCTG GGGAAGGTTT GCACTGTGCT GAAAAGCAAA GGATTTACAA TGGATGATGC     780

ACAAGATAAC AAAGGGAAAG AATATGCTAA GATACTCAGT TCTTGCAATC CCAATGCTAA     840

GGGAAGCATT GCTATGGACT ATTACAGTGA CAATCTTGAG AAGTTCTATG AAATGTTTGG     900

AGTCAAGAAA GAGGCCAAGA TTGCTGGTGT TGCATAAAAG CTTCTTTGTG TTAATTAAGA     960

GATGCATAAT ACTAAGTGTG GGGTACCGGG CCCCCCCTCG AGGTCGACGG TATCGATAAG    1020

CTTGATGTAC AGTCACCGGA TGTGCTTTCC GGTCTGATGA GTCCGTGAGG ACGAAACGGT    1080

ATGGTCTAAG GTTAAGCTCA CTAAGGAAAG CATTGTTGCT TTGTTGACAC AAGGCAAAGA    1140

CCTTGAGTTT GAGGAAGATC AGAATCTGGT AGCATTCAAC TTCAAGACTT TTTGTCTGGA    1200

AAACATCGAC CAGATCAAGA AGATGAGCGT TATTTCATGT CTGACATTCC TAAAGAATCG    1260

TCAGAGCATA ATGAAGGTTA TTAAGCAAAG CGATTTTACT TTTGGTAAAA TTACCATAAA    1320

GAAAACTTCA GACAGGATTG GAGGCACTGA CATGACCTTC AGAAGGCTTG ATAGCTTGAT    1380

CAGGGTCAGG CTTGTTGAAG AAACTGGGAA TTCTGAGAAT CTCAATACTA TCAAATCTAA    1440

GATTGCTTCC CATCCTTTGA TTCAAGCCTA TGGATTACCT CTCGATGATG CAAAGTCTGT    1500

GAGACTTGCC ATAATGCTGG GAGGTAGCTT ACCTCTTATT GCTTCAGTTG ATAGCTTTGA    1560

GATGATCAGT GTTGTCTTGG CTATATATCA GGATGCAAAA TACAAGGACC TCGGGATCGA    1620

CCCAAAGAAG TATGACACCA AGGAAGCCTT AGGAAAAGTT TGCACTGTGC TGAAAAGCAA    1680

AGCATTTGAA ATGAATGAAG ATCAGGTGAA GAAGGGGAAA GAGTATGCTG CTATACTTAG    1740

CTCCAGCAAT CCTAATGCTA AAGGGAGTGT TGCTATGGAA CATTACAGTG AAACTCTTAA    1800

CAAGTTCTAT GAAATGTTCG GGGTTAAAAA GCAGGCAAAA CTCGCAGAAC TTGCTTGACC    1860

GTCACCGGAT GTGCTTTCCG GTCTGATGAG TCCGTGAGGA CGAAACGGTA CCGAGCTCGC    1920

TGCAGAGCAA TTGTGTCAAT TTTATTCAAA AACATACTAC TCAGCAACAC AAATCATCAC    1980

ATTGCCAGGA TAAGTAACGA CTGCGGTCTA CAGAGTCGTA CTTTCTTACC TTGAATCACA    2040

TCTCTCGAGA GCGGTCTAGA TCTACACTGC AAAAATGTC TAAGGTCAAG CTCACCAGAG    2100

AGAACATTAT CTCTCTTCTA ACTCAGGCTG GAGAAATCGA GTTTGAAGAA GATCAAATCA    2160

AGGCTACATT CAACTTCGAA GACTTTTGCG GAGAAAATCT TGATTCAATC AAGAAAATGA    2220

GCATTACCTC ATGTTTGACT TTCCTGAAAA ATCGCCAGAG CATCATGAAA GTTGTGAACC    2280

TTTGTGATTT TACCTTTGGG AAAATCACAA TCAAAAAGAA TTCTGGAAGG GTTGGAGCTA    2340

ATGATATGAC TTTCAGAAGG CTTGATAGCA TGATAAGAGT TAAGCTGATT GAAGAAACTG    2400

GAAAAGCAGA AAAACCTTGCT ATTATCAAGT CTAAGATTGC CTCTCATCCT CTTGTTCAAG   2460

CTTATGGTCT GCCTCTGACA GATGCAAAGT CTGTAAGGCT TGCCATAATG CTAGGAGGTA    2520

GTATCCCTCT GATTGCTTCT GTGGACAGCT TTGAAATGAT CAGCATCATC CTTGCCATAT    2580

ACCAAGATGC TAAATATAAA GATCTTGGAA TTGAACCTTC GAAGTATAAC ACTAAAGAAG    2640

CTTTAGGAAA AGTCTGCACT GTGCTGAAAA GCAAAGGATT TACAATGGAT GAAGAGCAAG    2700
```

-continued

```
TGCAGAAAGG GAAAGAATAT GCTACAATAC TCAGCTCTTG CAATCCTAAT GCTAAAGGAA      2760

GCATTGCTAT GGAACATTAC AGTGAGCATC TTGACAAATT CTATGCAATG TTCGGAGTAA      2820

GGAAAGAAGC CAAAATTTCA GGTGTTGCAT GAAAGCTTCT TAAAATCTAT TTAAGAGATG      2880

AGTATTGTAG GCGGGATCC                                                   2899
```

(2) INFORMATION FOR SEQ ID NO:3:

(i) SEQUENCE CHARACTERISTICS:
  (A) LENGTH: 2917 base pairs
  (B) TYPE: nucleic acid
  (C) STRANDEDNESS: double
  (D) TOPOLOGY: unknown  (iii) HYPOTHETICAL: NO  (iii) ANTI-SENSE: NO  (vi) ORIGINAL SOURCE:
  (A) ORGANISM: Chimeric sequence  (xi) SEQUENCE DESCRIPTION: SEQ ID NO:3:

```
CTGCAGAGCA ATTGTGTCAA TTTTATTCAA AAACATACTA CTCAGCAACA CAAATCATCA        60

CATTGCCAGG ATAAGTAACG ACTGCGGTCT ACAGAGTCGT ACTTTCTTAC CTTGAATCAC       120

ATCTCTCGAG AGCGGTCTAG ATCTACACTG CCAAAAATGT CTAAGGTCAA GCTCACCAGA       180

GAGAACATTA TCTCTCTTCT AACTCAGGCT GGAGAAATCG AGTTTGAAGA AGATCAAATC       240

AAGGCTACAT TCAACTTCGA AGACTTTTGC GGAGAAAATC TTGATTCAAT CAAGAAAATG       300

AGCATTACCT CATGTTTGAC TTTCCTGAAA AATCGCCAGA GCATCATGAA AGTTGTGAAC       360

CTTTGTGATT TTACCTTTGG GAAAATCACA ATCAAAAGA ATTCTGGAAG GGTTGGAGCT        420

AATGATATGA CTTTCAGAAG GCTTGATAGC ATGATAAGAG TTAAGCTGAT TGAAGAAACT       480

GGAAAAGCAG AAAACCTTGC TATTATCAAG TCTAAGATTG CCTCTCATCC TCTTGTTCAA       540

GCTTATGGTC TGCCTCTGAC AGATGCAAAG TCTGTAAGGC TTGCCATAAT GCTAGGAGGT       600

AGTATCCCTC TGATTGCTTC TGTGGACAGC TTTGAAATGA TCAGCATCAT CCTTGCCATA       660

TACCAAGATG CTAAATATAA AGATCTTGGA ATTGAACCTT CGAAGTATAA CACTAAAGAA       720

GCTTTAGGAA AAGTCTGCAC TGTGCTGAAA AGCAAAGGAT TTACAATGGA TGAAGAGCAA       780

GTGCAGAAAG GGAAAGAATA TGCTACAATA CTCAGCTCTT GCAATCCTAA TGCTAAAGGA       840

AGCATTGCTA TGGAACATTA CAGTGAGCAT CTTGACAAAT TCTATGCAAT GTTCGGAGTA       900

AGGAAAGAAG CCAAAATTTC AGGTGTTGCA TGAAAGCTTC TTAAAATCTA TTTAAGAGAT       960

GAGTATTGTA GGGTACCCTT AACACTCAGT CTTACAAATC ATCACATTAA GAACCTAAGA      1020

AACGACTGCG GATACAGAG TTGCACTTTC GCACCTTGAG TTACATACGG TCAAAGCATA       1080

TAACAACTTT TACGATCATC ATGTCTAAGG TTAAGCTCAC TAAGGAAAGC ATTGTTGCTT      1140

TGTTGACACA AGGCAAAGAC CTTGAGTTTG AGGAAGATCA GAATCTGGTA GCATTCAACT      1200

TCAAGACTTT TTGTCTGGAA AACATCGACC AGATCAAGAA GATGAGCGTT ATTTCATGTC      1260

TGACATTCCT AAAGAATCGT CAGAGCATAA TGAAGGTTAT TAAGCAAAGC GATTTTACTT      1320

TTGGTAAAAT TACCATAAAG AAAACTTCAG ACAGGATTGG AGGCACTGAC ATGACCTTCA      1380

GAAGGCTTGA TAGCTTGATC AGGGTCAGGC TTGTTGAAGA AACTGGGAAT TCTGAGAATC      1440

TCAATACTAT CAAATCTAAG ATTGCTTCCC ATCCTTTGAT TCAAGCCTAT GGATTACCTC      1500

TCGATGATGC AAAGTCTGTG AGACTTGCCA TAATGCTGGG AGGTAGCTTA CCTCTTATTG      1560

CTTCAGTTGA TAGCTTTGAG ATGATCAGTG TTGTCTTGGC TATATATCAG GATGCAAAAT      1620
```

-continued

```
ACAAGGACCT CGGGATCGAC CCAAAGAAGT ATGACACCAA GGAAGCCTTA GGAAAAGTTT    1680

GCACTGTGCT GAAAAGCAAA GCATTTGAAA TGAATGAAGA TCAGGTGAAG AAGGGGAAAG    1740

AGTATGCTGC TATACTTAGC TCCAGCAATC CTAATGCTAA AGGGAGTGTT GCTATGGAAC    1800

ATTACAGTGA AACTCTTAAC AAGTTCTATG AAATGTTCGG GGTTAAAAAG CAGGCAAAAC    1860

TCGCAGAACT TGCTTGAAAG CAGCTGTAAG TTAAATTATA AAAAAGCCTA TAAATATATA    1920

AAGCTTATCG ATACCGTCGA CCTCGAGGGG GGGCCCGGTA CCGAGCTCGG TACCCGGGGA    1980

TCCACCATGG GAAATGACAC AATCGATGCA GGAGGAAGCA CTAAGAAAGA TGCAAAACAA    2040

GAGCAAGGTA GCATTCAACC AAATCTCAAC AAGGAAAAGG TAAAGGACGT GAATGTTGGA    2100

ACATCTGGAA CTCACACTGT GCCACGAATT AAAGCTATCA CGTCCAAAAT GAGAATGCCC    2160

AAGAGTAAGG GTGCAACTGT ACTAAATTTG GAACACCTAC TCGAGTATGC TCCACAGCAA    2220

ATTGAAATCT CAAATACTCG AGCAACTCAA TCACAGTTTG ATACATGGTA TGAAGCAGTA    2280

CAACTTGCAT ACGACATAGG AGAAACTGAA ATGCCAACTG TGATGAATGG GCTTATGGTT    2340

TGGTGCATTG AAAATGGAAC CTCGCCAAAT ATCAATGGAG TTTGGGTTAT GATGGATGGA    2400

GATGAACAAG TCGAATACCC AGTGAAACCA ATCGTTGAGA ATGCAAAACC AACACTTAGG    2460

CAAATCATGG CACATTTCTC AGATGTTGCA GAAGCGTATA TAGAAATGCG CAACAAAAG    2520

GAACCATATA TGCCACGATA TGGTTTAGTT CGTAATCTGC GCGATGGAAG TTTGGCTCGC    2580

TATGCTTTTG ACTTTTATGA AGTTACATCA CGTACACCAG TGAGGGCTAG AGAGGCACAC    2640

ATTCAAATGA AGGCCGCAGC TTTAAAATCA GCTCAATCTC GACTTTTCGG ATTGGATGGT    2700

GGCATTAGTA CACAAGAGGA AAACACAGAG AGGCACACCA CCGAGGATGT TTCTCCAAGT    2760

ATGCATACTC TACTTGGAGT GAAGAACATG TGATTGTAGT GTCTTTCCGG ACGATATATA    2820

GATATTTATG TTTGCAGTAA GTATTTTGGC TTTTCCTGTA CTACTTTTAT CGTAATTAAT    2880

AATCGTTTGA ATCAGATCCT CTAGAGTCCA CCTGCAG                             2917
```

(2) INFORMATION FOR SEQ ID NO:4:

(i) SEQUENCE CHARACTERISTICS:
        (A) LENGTH: 75 base pairs
        (B) TYPE: nucleic acid
        (C) STRANDEDNESS: unknown
        (D) TOPOLOGY: unknown     (iii) HYPOTHETICAL: NO     (iii) ANTI-SENSE: NO     (vi) ORIGINAL SOURCE:
        (A) ORGANISM: Primer     (xi) SEQUENCE DESCRIPTION: SEQ ID NO:4:

```
TGTGGTACCG TCACCGGATG TGCTTTCCGG TCTGATGAGT CCGTGAGGAC GAAACGGTAT    60

GGTCTAAGGT TAAGC                                                     75
```

(2) INFORMATION FOR SEQ ID NO:5:

(i) SEQUENCE CHARACTERISTICS:
        (A) LENGTH: 73 base pairs
        (B) TYPE: nucleic acid
        (C) STRANDEDNESS: unknown
        (D) TOPOLOGY: unknown     (iii) HYPOTHETICAL: NO     (iii) ANTI-SENSE: NO -continued (vi) ORIGINAL SOURCE:
    (A) ORGANISM: Primer (xi) SEQUENCE DESCRIPTION: SEQ ID NO:5:

ATAGGTACCG TTTCGTCCTC ACGGACTCAT CAGACCGGAA AGCACATCCG GTGACGGTCA    60

AGCAAGTTCT GCG                                                      73

VIRUS RESISTANT OR TOLERANT CELLS

The present invention relates to cells having a genetically engineered reduced susceptibility to viruses, processes for obtaining such cells, and genetic material capable of generating such reduced susceptibility. In a preferred embodiment the cells are plant cells.

Numerous attempts have been made to engineer viral resistance into plants by inserting DNA-containing vectors into acceptor plant tissue, which DNA is capable of encoding viral proteins in the thus transformed plant. The viral protein may confer resistance to an invading virus comprising a viral protein substantially the same as that encoded by the introduced DNA. Other attempts at engineering virus resistance in plants use anti-sense RNA which relies on the introduction of DNA encoding an RNA strand which is complementary to the RNA of an invading virus and thus interferes with the replication thereof. Plants displaying a broad degree of reduced susceptibility, i.e. to more than one viral type, or a greater degree of reduced susceptibility to a particular virus type, are highly desirable.

Resistance in plants to multiple virus types may be obtained by transforming plant tissue with DNA constructs made up of individual blocks of genetic elements, each element consisting essentially of three components:

(i) promoter
(ii) virus resistance conferring genetic element
(iii) terminator.

However, such constructs require the building in of many promoters and terminators and typically suffer from genetic instability.

The present invention provides inter alia, novel nucleotide sequences which can be used in the production of eukaryotic cells—particularly plant cells—which exhibit an improved resistance or tolerance to viruses. Such improvements surprisingly correlate primarily with the levels of the RNA and sub-sequences thereof encoded by the nucleotide sequence of the invention, rather than the levels of the translation products of such RNA. Indeed, improved resistance or tolerance may be obtained by transcription of the present inventive nucleotide sequences in eukaryotic cells, substantially in the absence of the translation of such transcription products.

According to the present invention there is provided a nucleotide sequence (nucleotide sequence according to the invention) comprising a transcriptional regulatory sequence and a sequence contiguous therewith and under the transcriptional control thereof, which contiguous sequence encodes an RNA which consists of a plurality of sub-sequences, characterized in that at least two of the sub-sequences have the sequences of viral RNAs and the RNA contains at least one translational stop codon located upstream of the 3' terminal sub-sequence.

Each of the sub-sequences may be responsible for conferring a reduced susceptibility to a virus in plant cells or for conferring an enhanced reduced susceptibility to a single virus type in plant cells. Such sub-sequences need not necessarily be capable of encoding protein, and it is preferred that at least one of them is incapable of encoding protein as a consequence of the RNA lacking a translational start codon at the 5' thereof and/or the contiguous sequence encoding a second sub-sequence down stream from a first sequence, the second sequence defining a translational reading frame which is out of phase with that defined by the first sub-sequence.

The said nucleotide sequence may encode an RNA having any number of sub-sequences. It is preferred that the number of sub-sequences is between 2 and 7 (inclusive) and still more preferred that the number is likewise between 2 and 4.

At least one of the sub-sequences may be in an anti-sense configuration with respect to virus RNA. The contiguous sequence may encode mRNA.

It is preferred that at least one of the sub-sequences is a cistron. By "cistron" is meant an RNA which contains a translation open reading frame, i.e. one that comprises a translation start codon, protein encoding sequence and a translation stop codon.

It is preferred that the RNA encoded by the contiguous sequence comprises at least one ribozyme (or other cleavage site) between two of the sub-sequences so that the RNA can be cleaved into regions comprising the said sub-sequences, or even into the sub-sequences per se. Except in the case of the most 5' of the sub-sequences contained within the RNA encoded by the contiguous sequence, the nucleotide sequences resulting from such cleavage will not contain a 5' cap or a ribosome binding site and will thus not be translated when present in a Eukaryotic cell.

It is more preferred that at least one of the subsequences encodes a viral coat protein or a viral nucleocapsid protein, for example, the nucleocapsid (N) protein of a tospovirus such tomato spotted wilt virus (TSWV), tomato chlorotic spot virus (TCSV), groundnut ringspot virus (GRSV), groundnut bud necrosis virus (GBNV), or Impatiens necrotic spot virus (INSV). Other viral proteins which may be encoded by the sub-sequences present in the RNA encoded by the contiguous sequence include viral replicases, movement proteins and the like derived from virus sources such as tospoviruses, potyviruses, potexviruses, tobamoviruses, luteoviruses, cucumoviruses, bromoviruses, closteorviruses, tombusviruses and furoviruses.

The invention still further provides a nucleotide sequence which is similar to the above disclosed sequence. By "similar" is meant a test sequence which is capable of hybridizing to a sequence which is complementary to the inventive nucleotide sequence. When the test and inventive sequences are double stranded the nucleic acid constituting the test sequence preferably has a TM within 20° C. of that of the inventive sequence. In the case that the test and inventive sequences are mixed together and denatured simultaneously, the TM values of the sequences are preferably within 10° C. of each other. More preferably the hybridization is performed under stringent conditions, with either the test or inventive DNA preferably being supported. Thus either a denatured test or inventive sequence is preferably first bound to a support and hybridization is effected for a specified period of time at a temperature of between 50 and 70° C. in double strength citrate buffered saline containing 0.1%SDS followed by rinsing of the support at the same temperature but with a buffer having a reduced SC concentration. Depending upon the degree of stringency required, and thus the degree of similarity of the sequences, such reduced concentration buffers are typically single strength SC containing 0.1%SDS, half strength SC containing 0.1%SDS and one tenth strength SC containing 0.1%SDS. Sequences having the greatest degree of similarity are those the hybridization of which is least affected by washing in buffers of reduced concentration. It is most preferred that the test and inventive sequences are so similar that the hybridization between them is substantially unaffected by washing or incubation in one tenth strength sodium citrate buffer containing 0.1%SDS.

The invention still further provides a nucleotide sequence which is complementary to one which hybridizes under stringent conditions with the above disclosed nucleotide sequences.

The invention also provides a DNA construct comprising the nucleotide sequence according to the invention, as well as a biological vector comprising the said sequence or construct. The biological vector may be a virus or a bacterium, such as *Agrobacterium tumefaciens*, for example, and the construct advantageously further encodes protein having herbicide resistance, plant growth-promoting, anti-fungal, anti bacterial, and/or anti-nematode properties.

The invention still further provides eukaryotic cells, such as plant cells (including protoplasts) for example, containing the said nucleotide sequence, construct or vector.

The invention still further provides plants comprising such plant cells, the progeny of such plants which contain the sequence stably incorporated and hereditable in a Mendelian manner, and/or the seeds of such plants or such progeny. Such plants include field crops, vegetables and fruits including tomato, pepper, melon, lettuce, cauliflower, broccoli, cabbage, brussels sprout, sugar beet, corn, sweetcorn, onion, carrot, leek, cucumber, tobacco, alfalfa, aubergine, beet, broad bean, celery, chicory, cow pea, endive, gourd, groundnut, papaya, pea, peanut, pineapple, potato, safflower, snap bean, soybean, spinach, squashes, sunflower, sorghum, water-melon and the like; and ornamental crops including Impatiens, Begonia, Petunia, Pelargonium, Viola, Cyclamen, Verbena, Vinca, Tagetes, Primula, Saint Paulia, Ageratum, Amaranthus, Anthirrhinum, Aquilegia, Chrysanthemum, Cineraria, Clover, Cosmo, Cowpea, Dahlia, Datura, Delphinium, Gerbera, Gladiolus, Gloxinia, Hippeastrum, Mesembryanthemum, Salpiglossis, Zinnia, and the like.

The invention still further provides the use of the sequence according to the invention,—whether "naked" or present in a DNA construct or biological vector—in the production of virus resistant or tolerant eukaryotic cells. By "resistant" is meant a cell which exhibits substantially no phenotypic changes as a consequence of infection with the virus. By "tolerant" is meant a cell which, although it may exhibit some phenotypic changes as a consequence of infection with a virus, does not have a substantially decreased reproductive capacity or substantially altered metabolism. Such use leads to the production of morphologically normal virus resistant or tolerant whole plants.

The invention still further provides a method of inducing resistance or tolerance to viruses in eukaryotic cells comprising introducing into such cells a nucleotide sequence according to the invention, or a construct or vector containing it. It is preferred that the cells are plant cells as indicated above.

The invention still further provides a method of inhibiting the production of at least one enzyme in a eukaryotic cell comprising introducing into the said cell a nucleotide sequence comprising a transcriptional regulatory sequence and a sequence contiguous therewith and under the transcriptional control thereof, which contiguous sequence encodes an RNA which consists of a plurality of sub-sequences, characterized in that the RNA encoded by the contiguous sequence contains at least one translational stop codon located upstream of the 3' terminal sub-sequence. In a further embodiment of the method, at least one of the sub-sequences is in an anti-sense configuration with respect to the coding sequence in the host cell mRNA which encodes the said enzyme. The enzyme may be of viral origin and present in the cell as a consequence of the viral infection thereof.

The invention will be further apparent from the following description taken in conjunction with associated drawings and sequence listings.

SEQ ID No. 1 shows a DNA sequence encoding the nucleocapsid proteins of GRSV, TSWV, and TCSV; SEQ ID No. 2 shows a DNA sequence substantially similar to that given in SEQ ID No. 1, except that each of the sub-sequences encoding the nucleocapsid proteins is bordered by a ribozyme sequence rendering the RNA encoded by the DNA sequence susceptible to cleavage at pre-determined sites; SEQ ID No. 3 shows a DNA sequence encoding TCSV and TSWV nucleocapsid proteins and the coat protein of potato virus Y$^n$ (PVY); SEQ ID No. 4 shows a first primer sequence designated ZUP422 (see below) and SEQ ID. No 5 shows a second primer sequence designated ZUP423 (see below).

Examples of the nucleotide sequences of the invention are provided below. These examples relate to the production of virus resistant or tolerant tomato plants. Tomato plants may be attacked by both the cucumber mosaic virus (CMV) and the tomato spotted wilt virus (TSWV). Enhanced resistance or tolerance to these viruses may be produced in a number of ways by introducing various embodiments of the nucleotide sequence of the invention into the plants, or the progenitor material thereof.

1. The contiguous sequence in the nucleotide sequence of the invention may encode an mRNA which consists—in the 5' to 3' direction—of (i) a translation start codon, (ii) the coding region of the nucleocapsid protein of TSWV, (iii) a translation stop codon, (iv) optionally a further start codon, (v) the coding region of the CMV replicase and (vi) optionally a further stop codon. When such a sequence is introduced into the cells of tomato plants, the sequence encoding the mRNA is transcribed. The region of the thus transcribed mRNA which encodes the TSWV nucleocapsid protein is translated, whilst the region of the mRNA which encodes the CMV replicase is not translated as a result of translation ceasing at the stop codon on the 3' side of the coding region of the TSWV nucleocapsid protein.

2. The contiguous sequence in the nucleotide sequence of the invention may encode an mRNA which consists—in the 5' to 3' direction—of (i) a translation start codon, (ii) the coding region of the CMV coat protein, (iii) a translation stop codon, (iv) optionally a further start codon, (v) a region encoding the nucleocapsid protein of TSWV and (vi) optionally a further stop codon. When such a sequence is introduced into the cells of tomato plants, the sequence encoding the mRNA is transcribed. The region of the thus transcribed mRNA which encodes the CMV coat protein is translated, whilst the region of the mRNA which encodes the nucleocapsid protein of TSWV is not translated as a result of translation ceasing at the stop codon on the 3' side of the region encoding the CMV coat protein.

3. The contiguous sequence in the nucleotide sequence of the invention may encode an RNA which consists—in the 5' to 3' direction—of (i) the coding region of the CMV coat protein, (ii) a translation stop codon, (iii) optionally a further start codon, (iv) a region encoding the nucleocapsid protein of TSWV and (v) optionally a further stop codon. When such a sequence is introduced into the cells of tomato plants, the sequence encoding the RNA is transcribed, but the RNA is not translated inter area because the first cistron does not contain a translation stare codon upstream of the translational stop codon, even assuming that the RNA contains a 5' cap to which ribosomes could bind. The skilled man is aware that eukaryotic cells do not translate second and subsequent cistrons in polycistronic RNA if the first cistron possesses a stop codon.

4. The contiguous sequence in the nucleotide sequence of the invention may encode an mRNA which consists—in the 5' to 3' direction—of (i) a translational start codon (ii) the coding region of the CMV coat protein, (iii) a translation stop codon, (iv) optionally a further start codon, (v) a region encoding the nucleocapsid protein of TSWV in an antisense configuration with respect to mRNA which encodes the TSWV nucleocapsid protein, (vi) optionally a further stop codon. When such a sequence is introduced into the cells of tomato plants, the sequence encoding the mRNA is transcribed. The region of the thus transcribed mRNA which encodes the CMV coat protein is translated, whilst the region of the mRNA which encodes the nucleocapsid protein of TSWV is not translated as a result of translation ceasing at the stop codon on the 3' side of the region encoding the CMV coat protein. The region of the non-translated A which contains the said anti-sense RNA is capable of base pairing with the mRNA encoding the TSWV nucleocapsid protein.

It will be appreciated that the contiguous sequence may encode an RNA comprising sub-sequences, two or more of which have sequences derived from a common virus type, so that still greater resistance to virus infection can be generated. For example:

6. The contiguous sequence in the nucleotide sequence of the invention may encode an mRNA which consists—in the 5' to 3' direction—of (i) a translational start codon (ii) the coding region of the TSWV replicase, (iii) a translation stop codon, (iv) optionally a further start codon, (v) a region encoding the nucleocapsid protein of TSWV, (vi) optionally a further stop codon. When such a sequence is introduced into the cells of tomato plants, the sequence encoding the mRNA is transcribed. The region of the thus transcribed mRNA which encodes the replicase is translated, whilst the region of the mRNA which encodes the nucleocapsid protein of TSWV is not translated as a result of translation ceasing at the stop codon on the 3' side of the region encoding the TSWV replicase.

7. The contiguous sequence in the nucleotide sequence of the invention may encode an mRNA which consists—in the 5' to 3' direction—of (i) a translational start codon (ii) a region encoding a first nucleocapsid protein of TSWV, (iii) a translation stop codon, (iv) optionally a further start codon, (v) a region encoding a second nucleocapsid protein of TSWV, (vi) optionally a further stop codon. When such a sequence is introduced into the cells of tomato plants, the sequence encoding the mRNA is transcribed. The region of the thus transcribed mRNA which encodes the first nucleocapsid protein is translated, whilst the region of the mRNA which encodes the second nucleocapsid protein is not translated as a result of translation ceasing at the stop codon on the 3' side of the region encoding the first protein. If desirable, the translational start codon on the 5' side of the region encoding the first nucleocapsid protein may be deleted.

The following discussion details the production of nucleotide sequences according to the invention, their insertion into appropriate vectors, transformation of plant material with such vectors, and the regeneration of such transformed material into virus resistant or tolerant morphologically normal whole plants.

Cultivation of plant material and bacterial strains, and generation of vectors Cultivars of *Nicotinic tabacum* and *Lycopersicon esculentum,* used in plant transformation studies, are grown under standard greenhouse conditions. Axenic explant material is grown on standard MS media [Murashige and Skoog (1962). Physiol. Plant 15:473] containing phytohormones and sucrose at appropriate concentrations.

*E. coli* is grown on rotary shakers at 37° C. in standard LB-medium. *Agrobacterium tumefaciens* strains are grown at 28° C. in Min. A medium supplemented with 0.1% glucose [Ausubel et al., (1987). Current Protocols in Molecular Biology, Green Publishing Associates and Wiley Intersciences].

In all cloning procedures, *E. coli* strain JM83, (F, Δ (lac-pro), ara, rpsL, Ø80, dlacZM15) is used as the recipient for recombinant plasmids.

Binary vectors are conjugated to *Agrobacterium tumefaciens* strain LBA 4404, a strain containing the Ti-plasmid vir region, [Hoekema et al. (1983) Nature 303:179 ] in standard triparental matings using *E. coli* HB101 containing the plasmid pRK2013 as a helper strain [Figurski and Helsinki, (1979) PNAS 76:1648]. Appropriate *A. tumefaciens* recipients are selected on media containing rifampicin (50 μg/ml) and kanamycin (50 μg/ml).

Cloning of fragments in the vectors pUC19 [Yanish-Perron et al. (1985)Gene 33:103], pBluescript (Stratagene), pBIN19 [Bevan et al. (1984) Nucl. Acids Res. 12:8711] or derivatives thereof, restriction enzyme analysis of DNA, transformation of *E. coli* recipient strains, isolation of plasmid DNA on small as well as large scale, nick-translation, in vitro transcription, DNA sequencing, Southern blotting and DNA gel electrophoresis are performed according to standard procedures [Maniatis et al. (1982) Molecular Cloning: A Laboratory Manual. Cold Spring Harbor Laboratory, New York; Ausubel et al. supra, (1987)].

Collection of cDNA clones to Nucleocapsid (N) genes of different tospoviruses and to the Coat Protein (CP) gene of PVY A recombinant pUC19-derived plasmid containing the TSWV N gene is described by De Haan et al. (1990) J. Gen. Virology 71:001. Recombinant pBluescript-derived plasmids containing the TCSV N gene, and GRSV N genes are described by De Avila et al. (1993) J. Gen. Virology 74:153. A recombinant pUC19-derived plasmid containing the PVY CP gene is described by Van der Vlugt (1992). PhD thesis, Agricultural University Wageningen, The Netherlands, Ch4; pages 45–47.

Construction of expression vectors pZU-C and pZU-D

Expression vectors PZU-C and pZU-D are derivatives of pZU-B described in European patent publication No. EP-A 426 195. The unique Sma1 cloning site between the TMV Ω sequence and the NOS terminator is replaced using standard laboratory techniques [Maniatis et al supr, (1982); Ausubel et al (1987) surpra] by an Nco1 cloning site, yielding pZU-C. pZU-C is linearized with Pst1 and treated with T4 DNA polymerase to obtain blunt ends. BamH1 linkers are ligated and the plasmid is digested with BamH1 and subsequently recircularized using T4 DNA ligase resulting in recombinant plasmid pZU-D.T The recombinant plasmids pZU-C and pZU-D contain the 35S HincII-TMV Ω fusion (35S-Ω), unique NcoI, Pst1 (pZU-C) or NcoI, BamHI (pZU-D) sites and the NOS terminator.

Figure 1:
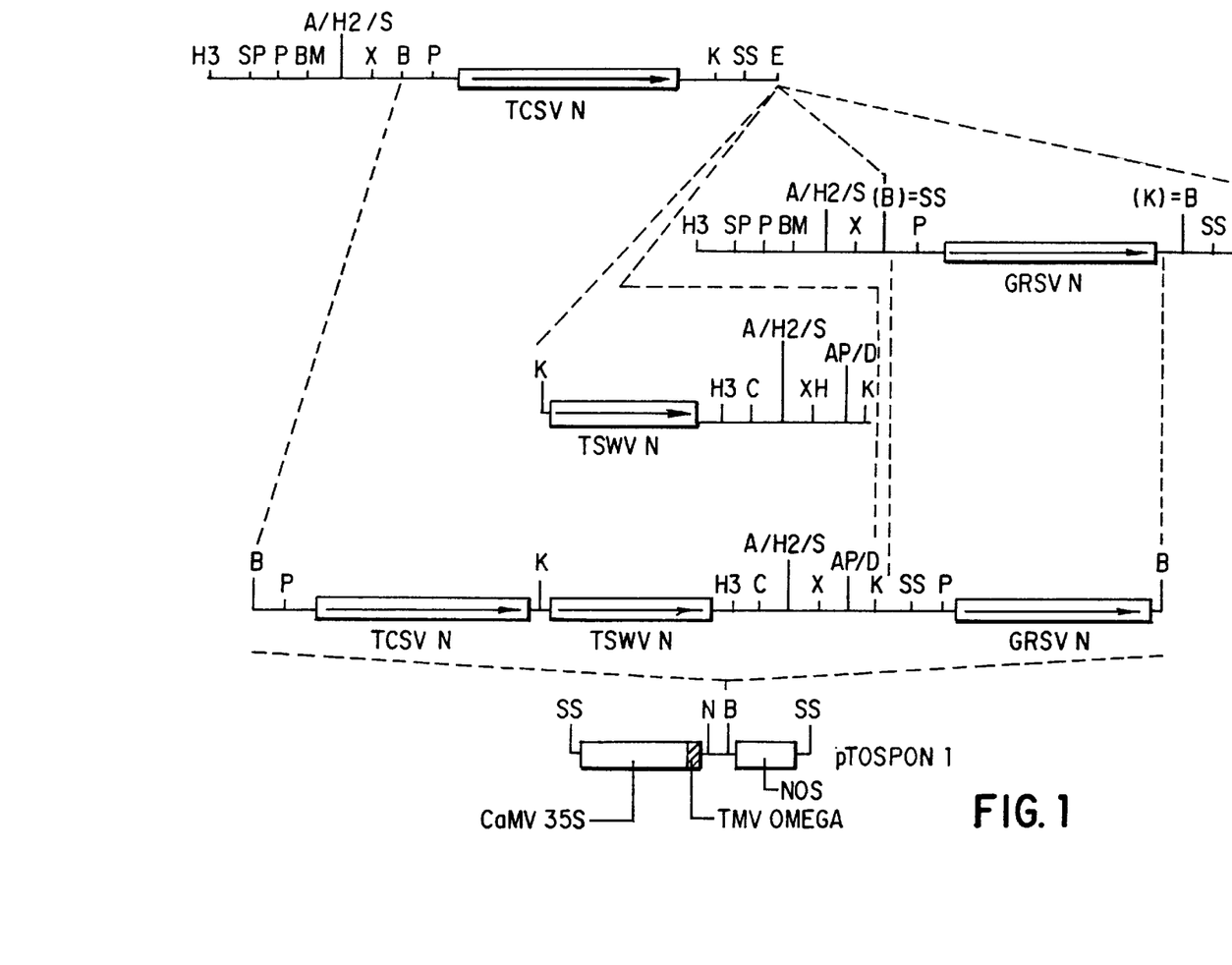
FIG. 1 shows a schematic representation of constructs comprising possible nucleotide sequences according to the invention, in which the contiguous sequence encodes an RNA comprising sub-sequences encoding the nucleocapsid proteins of TCSV, TWSV and GRSV.

Construction of a plant transformation vector containing three tospoviral N genes The recombinant pUC19-derived plasmid containing the GRSV N gene is linearized with BamH1 and treated with T4 DNA polymerase to obtain blunt ends. Sst1 linkers are ligated and the plasmid is digested with Sst1 and subsequently recircularized using T4 DNA ligase. The resulting plasmid is then linearized with Kpn1 and treated with T4 DNA polymerase to obtain blunt ends. BamH1 linkers are ligated and the plasmid is digested with BamH1 and subsequently recircularized using T4 DNA ligase resulting in recombinant plasmid GRSV N (FIG. 1), containing the GRSV N gene (nucleotides 1986 through to 2953 SEQ ID No. 1). Plasmid GRSV N is subjected to Sst1 digestion and the fragment containing the GRSV N gene is separated electrophoretically and purified from the gel using an NA-45 (Schleicher and Schüll) DEAE membrane and cloned into Sst1 linearized TCSV N (a pBluescript-derived recombinant plasmid) containing the TCSV N gene (nucleotides 7 through to 981 SEQ ED No. 1) resulting in TCSV N—GRSV N. Plasmid TSWV N is subjected to Kpn1 digestion and the fragment containing the TSWV N gene (nucleotides 988 through to 1930 SEQ ID No. 1) is separated electrophoretically and purified from the gel using an NA45 DEAE membrane and cloned into Kpn1 linearized TCSV N—GRSV N, resulting in the recombinant plasmid TCSV N—TSWV N—GRSV N (FIG. 1) Plasmid TCSV N—TSWV N—GRSV N (SEQ ID No. 1) is subjected to BamH 1 digestion and the fragment containing the tospoviral N genes, is separated electrophoretically and purified from the gel using an NA45 DEAE membrane and cloned into BamH1 linearized pZU-D, resulting in pTOSPON 1 (FIG. 1). The nucleotide sequence containing the 35S-Ω promoter, the tosporival N genes and the NOS terminator is excised from the plasmid pTOSPON 1 via a partial Sst1 digestion. The isolated gene cassette is then inserted into the Sst1 linearized pBIN19 to create the binary transformation vector pBIN-TOSPON 1.

Construction of a plant transformation vector containing three tospoviral N genes flanked by ribozyme sequences The nucleotide sequence of DNA encoding the RNA which encodes the three tospoviral nucleocapsid sequences contains ribozyme sequences and is depicted in SEQ ID No. 2.

Two primers are constructed, ZUP422 (depicted in SEQ ID No. 4) and ZUP423 (depicted in SEQ ID No. 5) containing Kpn1 cloning sites, the active ribozyme sequence of the tobacco ringspot virus satellite RNA and 17 nucleotides overlap to the coding region of the TSWV N gene. The primers are used to PCR amplify the TSWV N gene using pTOSPON as a template. The PCR fragment is made blunt-ended by treatment with T4 DNA polymerase and subsequently cloned in the EcoR V site of plasmid pSK+. Clones are obtained, which contain a Kpn1 insertion of the expected size. Sequence analysis reveals that the Kpn1 site originating from primer ZUP422 is destroyed. Therefore, the Kpn1 site located on the multilinker of pSK+, together with the Kpn1 site originating from primer ZUP423 are used to replace the TSWV N gene (as a Kpn 1 fragment) located on the recombinant plasmid TCSV N—TSWV N GRSV N (see above), yielding plasmids TCSV N—ribozyme—TSWV N—ribozyme—GRSV N and TCSV N—ribozyme—TSWV N antisense—ribozyme—GRSV N. These plasmids are linearized with BamH1 and used as templates to produce run-off transcripts with T7 RNA polymerase. Polyacrylamide gel electrophoresis reveals that the primary transcripts are immediately and completely cleaved to yield the separate sense and/or tospoviral N gene molecules. Plasmids TCSV N—ribozyme—TSWV N—ribozyme—GRSV N and TCSV N—ribozyme—TSWV N antisense— ribozyme— GRSV N (SEQ ID No. 2) are subjected to BamH1 digestion and the fragments containing the tospoviral N genes are separated electrophoretically and purified from the gel using an NA-45 DEAE membrane and cloned into BamH1 linearized pZU-D, resulting in pTOSPON-ribo1 and pTOSPON-ribo2 (FIG. 1) respectively. The nucleotide sequences containing the 35S-Ω promoter, the tosporival N genes bordered by ribozymes, and the NOS terminator are excised from the plasmids via a partial Sst1 digestion. The isolated gene cassettes are then inserted into the Sst1 linearized pBIN19 to create the binary transformation vectors pBIN-TOSPON-ribo1 and pBIN-TOSPON-ribo2 respectively.

Both constructs are transferred to plants yielding 23 pBIN-TOSPON-ribo1 and 17 pBIN-TOSPON-ribo2 transformants. The progeny of the transformants is challenged with the various tospoviruses and found to exhibit an improved resistance or tolerance thereto, in comparison with non-transformed controls.

Figure 2:
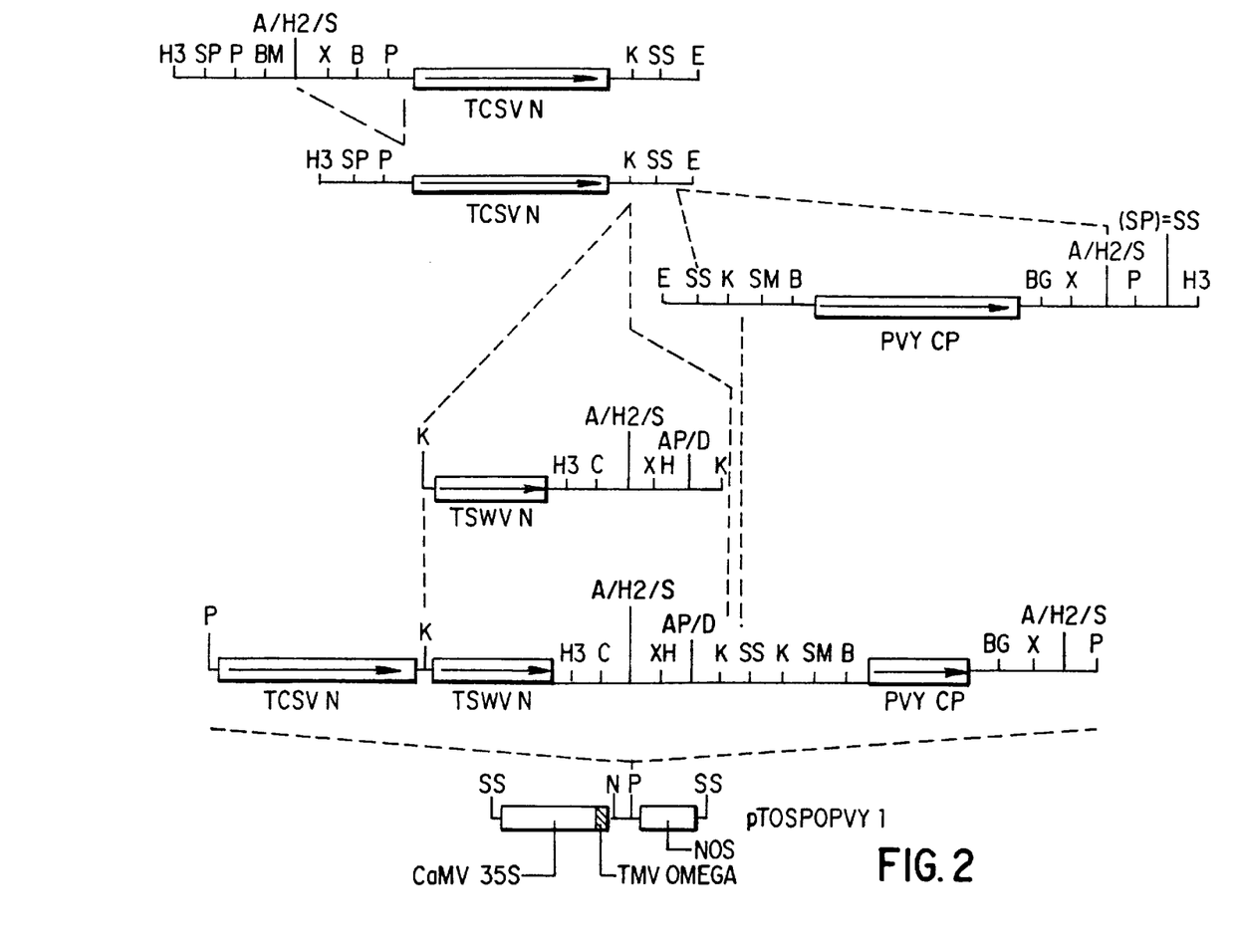
FIG. 2 shows a schematic representation of constructs comprising possible nucleotide sequences according to the invention, in which the contiguous sequence encodes an RNA comprising sub-sequences encoding the nucleocapsid proteins of TCSV and TSWV and the coat protein of PVY.

Construction of a plant transformation vector containing two tosporival N genes and the CP gene of PVY Plasmid TCSV N is subjected to digestion with Pst1 and the large fragment containing the TCSV N gene and pUC19 is separated electrophoretically and purified from the gel using a DEAE membrane (NA-45, Schleicher and Schüll) and recircularized using T4 DNA ligase, resulting in TCSV N (FIG. 2). The recombinant pUC19-derived plasmid containing the pVY CP gene (nucleotides 1984 through to 2899 SEQ ID No. 3) is linearized with Sph1 and treated with T4 DNA polymerase to obtain blunt ends. Sst1 linkers are ligated and the plasmid is digested with Sst1 and subsequently re-circularized using T4 DNA ligase, resulting in recombinant plasmid PVY CP (FIG. 2). Plasmid PVY CP is subjected to Sst1 digestion and the fragment containing the PVY CP gene is separated electrophoretically and purified from the gel using an NA-45 DEAE membrane and cloned into Sst1 linearized TCSV N, resulting in TCSV N-PVY CP. Plasmid TSWV N is subjected to Kpn1 digestion and the fragment containing the TSWV N gene (FIG. 2) is separated electrophoretically and purified from the gel using an NA-45 DEAE membrane and cloned into Kpn1 linearized TCSV N—PVY CP, resulting in the recombinant plasmid TCSV N—TSWV N—PVY CP. Plasmid TCSV N—TSWV N—PVY CP is subjected to Pst1 digestion and the fragment containing the tospoviral N genes and the PVY CP gene is separated electrophoretically and purified from the gel using an NA-45 DEAE membrane and cloned into Pst1 linearized pZU-C, resulting in pTOSPOPVY 1 (FIG. 2). The gene cassette containing the 35S-Ω promoter, TCSV and TSWV N genes, the PVY CP gene and the NOS terminator is excised from the plasmid pTOSPOPVY 1 via a partial Sst1 digestion. The isolated gene cassette is then inserted into the Sst1 linearized pBIN19 to create the binary transformation vector pBIN-TOSPOPVY 1.

Introduction of binary vectors to tobacco and tomato plant material

Methods to transfer binary vectors to plant material are known to a person skilled in the art. Variations in procedures exist due to differences in Agrobacterium strains used, different sources of explant material, differences in regeneration systems, and on the cultivar of plant species employed.

Binary plant transformation vectors as described above are employed in plant transformation experiments according to the following procedures. Binary vector constructs are transferred by tri-parental mating to an acceptor *Agrobacterium tumefaciens* strain, followed by southern analysis of exconjugants for verification of proper transfer of the construct to the acceptor strain, inoculation and cocultivation of axenic explant material with *Agrobacterium tumefaciens* strain of choice, selective killing of the *Agrobacterium tumefaciens* used with appropriate antibiotics, selection of transformed cells by growing on selective media containing kanamycin, transfer of tissue to shoot-inducing media, transfer of selected shoots to root induction media, transfer of plantlets to soil, assaying for intactness of the construct by southern analyses of isolated total DNA from the transgenic plant, assaying for proper function of the inserted gene by northern analysis and/or enzyme assays and western blot analysis of proteins following methods as described by Ausubel et al. supra.

Expression of DNA sequences in tobacco and tomato plant cells

RNA is extracted from leaves of regenerated plants using the following protocol. 200 mg leaf material is ground to a fine powder in liquid nitrogen. 800 μl RNA extraction buffer (100 mM Tris-HC1 (pH 8,0), 500 mM NaCl, 2 mM EDTA, 200 nM β-Mercapto-ethanol, 0.4% SDS) is added and the homogenate extracted with phenol, and nucleic acids collected by alcohol precipitation. Nucleic acids are re-suspended in 0.5 ml 10 MM Tris-HCl (pH 8,0), 1 mM EDTA, and LiCl is added to a final concentration of 2 M, and left on ice for no longer than 4 hours. The RNA is collected by centrifugation and re-suspended in 400 μl 10 mM Tris-HCl (pH 8.0), 1 mM EDTA and then precipitated with alcohol. The RNA is then re-suspended in 50 μl 10 mM Tris-HCl (pH 8,0), 1 mM EDTA. PNAs are separated on glyoxal/agarose gels and blotted to Genescreen as described by van Grinsven et al. [(1986) Theor. Appl. Gen. 73:94–101]. Recombinant viral RNA sequences are detected using DNA or RNA probes labeled with [$^{32}$P], [$^{35}$S] or by using non-radioactive labeling techniques. Based on northern analysis, it is determined to what extent the regenerated plants express recombinant viral genes.

Plants transformed with recombinant viral DNA molecules are also subjected to Western blot analysis after inoculation of the plant with the respective virus. Proteins are extracted from leaves of transformed plants by grinding in sample buffer [Laemmli (1970) Nature 244:29] and a 50 μg portion of protein is subjected to electrophoresis in a 12.5% SDS-polyacrylamide gel. Separated proteins are transferred to nitrocellulose electrophoreteically as described by Towbin et al. [(1979) PNAS76:4350]. Transferred proteins are reacted with anti-serum raised against purified TCSV nucleocapsids. Based on the results of the Western analysis it is determined that transformed plants express TCSV protein.

Resistance of tobacco and tomato plants against tospoviral and/or potyviral infection Transformed plants are grown in the greenhouse under standard quarantine conditions in order to prevent any infections by undesirable pathogens. The transformants are self-pollinated and the seeds harvested. Progeny plants are analyzed for segregation of the inserted gene and are subsequently infected with TCSV, TSWV, and/or GRSV and PVY by mechanical inoculation. Tissue from plants systemically inected with these viruses is ground in 5 volumes of ice-cold inoculation buffer (10 mM phosphate buffer, containing 10 mM sodium sulphite) and rubbed in the presence of carborundum power on the first two fully extended leafs of approximately 5 week old seedlings. Inoculated plants are monitored for symptom development for 3 weeks after inoculation.

Plants containing TOSPON 1 (FIG. 1), pTOSPON-ribo1, pTOSPON-ribo2 or TOSPOPVY 1 (FIG. 2) sequences show reduced susceptibility to infection with TCSV, TSWV, and/or GRSV and PVY compared with untransformed control plants which show severe systemic symptoms within 7 days after inoculation with these viruses. Plants that resisted infection are self pollinated and the like resistance of the resulting S2 progeny is demonstrated.

It will be appreciated that the present invention is not limited to the above examples only, but includes all logical and obvious extensions of the embodiments of the invention disclosed herein as well as those specifically claimed. Thus the invention also includes the embodiments indicated in the next paragraph in the clauses numbered 1–12.

(1). Multigene DNA constructs comprising at least one non-structural gene wherein the multigene DNA is under the control of a single set of genetic regulatory elements. By "non-structural gene" is meant a gene capable of coding for a viral RNA molecule which is substantially incapable of encoding for a viral polypeptide or protein but which is nevertheless capable of conferring an RNA mediated reduced susceptibility of a plant virus in plant cells. (2). Constructs according to clause 1, wherein the at least one non-structural gene is a viral gene. (3). Multigene DNA constructs comprising at least one non-structural gene wherein the multigene DNA constructs are capable of giving rise to viral elements in plant cells which are capable of conferring a reduced susceptibility to plant viruses in plant cells, and wherein the multigene DNA is under the control of a single set of genetic regulatory elements. (4) Constructs according to clauses 2 to 3 comprising at least one viral non-structural gene and one viral structural gene. (5) Constructs according to any one of clauses 2 to 4 comprising at least two non-structural genes and no viral structural gene elements. (6). Constructs according to clause 5 comprising from 2 to 5 viral non-structural genes. (7). Constructs according to any one of clauses 1 to 3 comprising DNA capable of coding for viral RNA molecules of tospoviruses, potyviruses, potexviruses, tobamoviruses, luteoviruses, cucumoviruses, bromoviruses, closteroviruses, tombusviruses, and furoviruses. (8) Constructs according to clause 7, wherein the DNA codes for non-structural viral RNA molecules of nucleocapsid proteins, viral coat proteins, and non-structural viral proteins. (9). Plants comprising multigene DNA constructs of any one of clauses 1 to 3. (10). Plants according to clause 9 selected from the group comprising tomatoes, peppers, melons, lettuces, caulifowers, broccolis, cabbages, brussels sprouts, sugar beet, corn (maize), sweetcorn, onions, carrots, leeks, cucumbers, tobacco's alfalfa's, aubergines, beets, broad beans, celery's, chicory's, cow peas, endives, gourds, groundnuts, papayas, peas, peanuts, pineapples, potatoes, safflowers, snap beans, soybeans, spinaches, squashes, sunflowers, water-melons, and sorghums. (11). Plants according to clause 9 selected from the group ornamentals consisting essentially of Impatiens, IBegonias, Petumias, Pelargoniums (geraniums), Violas, Cyclamens, Verbenas, Vincas, Tagetes, Primulas, Saint Paulia's Ageratums, Amaranthuses, Anthirrhinums, Aquilegias, Chrysanthemums, Cineraria, Clovers, Cosmos's, Cowpeas, Dahlia's, Daturas, Delphiniums, Gerbera's, Gladioluses, Gloxinias, Hippeastrums, Mesembryanthemums, Salpiglossis, and Zinnias. (12). A method for obtaining plants displaying a reduced susceptibility to viruses which comprises: (a) inserting into the genome of a plant cell a DNA construct according to any one of clauses 1 to 8; (b) obtaining transformed cells; and (c) regenerating from the transformed cells genetically transformed plants.

---

I claim:

1. A nucleotide sequence comprising a transcriptional regulatory sequence and a sequence contiguous therewith and under the transcriptional control thereof, which contiguous sequence encodes an RNA which consists of a plurality of sub-sequences, wherein at least two of the sub-sequences have the sequences of viral RNAs and the RNA contains at least one translational stop codon located upstream of the 3' terminal sub-sequence.

2. A nucleotide sequence according to claim 1, wherein at least one of the sub-sequences is in an anti-sense orientation with respect to virus RNA.

3. A nucleotide sequence according to either of claims 1 or 2, wherein the contiguous sequence encodes mRNA.

4. A nucleotide sequence according to any one of the preceding claims, wherein at least one of the sub-sequences is a cistron.

5. A nucleotide sequence according to any one of the preceding claims, wherein the RNA encoded by the contiguous sequence comprises at least one ribozyme between two of the sub-sequences.

6. A nucleotide sequence according to any one of the preceding claims, wherein at least one of the sub-sequences encodes a viral coat protein or a viral nucleocapsid protein.

7. A nucleotide sequence according to any one of the preceding claims, wherein the contiguous sequence encodes an RNA which comprises at least one sub-sequence obtained from viruses selected from the group consisting of tospoviruses, potyviruses, potexviruses, tobamoviruses, luteoviruses, cucmoviruses, bromoviruses, closteroviruses, tombusviruses and furoviruses.

8. A DNA construct comprising the nucleotide sequence of any one of claims 1 to 7.

9. A vector comprising the nucleotide sequence of any one of claims 1 to 7, or the construct of claim 8.

10. A nucleotide sequence according to claim 6 wherein the sub-sequence encodes a viral nucleocapsid protein obtained from viruses selected from the group consisting of tomato spotted wilt virus, tomato chlorotic spot virus, groundnut ringspot, groundnut bud necrosis virus and Impatiens necrotic spot virus.

11. A nucleotide sequence according to claim 6 wherein the sub-sequence encodes a viral coat protein obtained from a cucumber mosaic virus or a potato virus Y.

12. The DNA construct according to claim 8, wherein the nucleotide sequence is SEQ ID No. 1.

13. The DNA construct according to claim 8 wherein the nucleotide sequence is SEQ ID No.2.

14. The DNA construct according to claim 8 wherein the nucleotide sequence is SEQ ID No.3.

15. A plant cell containing the nucleotide sequence according to any one of claims 1 to 7, the construct of claim 8 or the vector of claim 9.

16. A plant comprising the cells of claim 15, wherein the progeny of said plant includes the sequence stably incorporated therein and inhereditable in a Mendelian manner.

17. The seeds of the plant and the seeds of the plant progeny according to claim 16.

18. A method of producing a virus resistant or tolerant plant cell comprising the steps of introducing into a plant cell the sequence according to anv one of claims 1 to 7, the construct of claim 8, or the vector of claim 9, obtaining a transformed plant cell wherein the sequence, construct or vector is stably incorporated therein and said transformed plant cell is virus resistant or tolerant.

19. A method of producing morphologically normal virus resistant or tolerant whole plants comprising the steps of
   a. introducing into plant cells the sequence according to any one of claims 1 to 7, the construct of claim 8, or the vector of claim 9;
   b. obtaining transformed plant cells; and
   c. regenerating from the transformed plant cells genetically transformed plants wherein said transformed plants are morphologically normal virus resistant or tolerant whole plants.

20. A method of inducing resistance or tolerance to viruses in plant cells comprising the steps of; a) introducing into said plant cells a nucleotide sequence according to any one of claims 1 to 7 or a construct according to claim 8 or the vector according to claim 9.

21. A method of inhibiting the production of at least one enzyme in a plant cell comprising introducing into the said cell a nucleotide sequence comprising a transcriprional regulatory sequence and a sequence contiguous therewih and under transcriptional control thereof, which contiguous sequence encodes a RNA which consists of a plurality of subsequences, wherein the RNA encoded by the contiguous sequence contains at least one translational stop codon located upstream of the 3' terminal sub-sequence.

22. A method according to the preceding claim, wherein at least one of the sub-sequences is in an anti-sense orientation with respect to the coding sequence in the host cell mRNA which encodes the said enzymne.

23. A nucleotide sequence comprising a transcriptional regulatory sequence and a sequence contiguous therewith and under the transcriptional control thereof, which contiguous sequence encodes a mRNA which includes in the 5' to 3' direction (i) a translation start codon; (ii) a coding region selected from the group consisting of sequences encoding a nucleocapsid protein, a coat protein, and a viral replicase; (iii) a translation stop codon; (iv) optionally a second start codon; (v) a second coding region selected from the group consisting of sequences encoding a nucleocapsid protein in either the sense or antisense orientation, and a viral replicase; and (vi) optionally a second stop codon wherein the first coding region is translated and the second coding region is not translated as a result of the stop codon on the 3' side of the region encoding the second coding region.

24. A nucleotide sequence comprising,
   (i) transcriptional regulatory elements and
   (ii) a sequence contiguous with the transcriptional regulatory elements and under control thereof,
wherein the contiguous sequence encodes an RNA which consists of at least two sub-sequences and not more than seven sub-sequences and at least two of the sub-sequences have sequences of viral RNA which may encode a viral coat protein or a viral nucleocapsid protein and the RNA contains at least one translational stop codon located upstream of the 3' tennnal sub-sequence.

25. The sequence of claim 24 wherein the nucleocapsid protein is a tospovirus nucleocapsid protein of a virus selected from the group consisting of tomato spotted wilt virus, tomato chlorotic spot virus, groundnut ringspot virus, groundnut bud necrosis virus and impatiens necrotic spot virus.

26. The sequence of claim 24 wherein the coat protein is obtained from a cucumber mosaic virus or a potato virus Y.

27. The sequence of claim 24 wherein at least one of the sub-sequences is a cistron.

\* \* \* \* \*